United States Patent
Candi et al.

(10) Patent No.: US 9,568,467 B2
(45) Date of Patent: Feb. 14, 2017

(54) INHIBITORS OF MICRO-RNAS FOR USE FOR PREVENTING AND/OR ATTENUATING SKIN AGEING

(71) Applicant: CHANEL PARFUMS BEAUTE, Neuilly sur Seine (FR)

(72) Inventors: Eleonora Candi, Rome (IT); Gerry Melino, Rome (IT); Gaelle Saintigny, Paris (FR); Christian Mahe, Neuilly sur Seine (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 570 days.

(21) Appl. No.: 14/012,128

(22) Filed: Aug. 28, 2013

(65) Prior Publication Data
US 2014/0065250 A1    Mar. 6, 2014

(30) Foreign Application Priority Data

Aug. 29, 2012 (EP) .................................... 12306029

(51) Int. Cl.
| | |
|---|---|
| *C12Q 1/68* | (2006.01) |
| *G01N 33/50* | (2006.01) |
| *A61K 8/49* | (2006.01) |
| *A61K 8/60* | (2006.01) |
| *A61K 8/97* | (2006.01) |
| *A61Q 19/08* | (2006.01) |
| *C12Q 1/26* | (2006.01) |
| *C12Q 1/58* | (2006.01) |
| *C12Q 1/66* | (2006.01) |

(52) U.S. Cl.
CPC ........... *G01N 33/5044* (2013.01); *A61K 8/498* (2013.01); *A61K 8/602* (2013.01); *A61K 8/606* (2013.01); *A61K 8/97* (2013.01); *A61Q 19/08* (2013.01); *C12Q 1/26* (2013.01); *C12Q 1/58* (2013.01); *C12Q 1/66* (2013.01); *C12Q 1/6876* (2013.01); *G01N 33/5008* (2013.01); *A61K 2800/782* (2013.01); *C12Q 2600/148* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | | |
|---|---|---|---|---|
| 2011/0107440 A1* | 5/2011 | Pivarcsi | ............... | C12Q 1/6886 800/3 |
| 2011/0152352 A1* | 6/2011 | Hata | ..................... | C12N 15/111 514/44 A |
| 2011/0301091 A1* | 12/2011 | Giuliani | ............... | A61K 38/168 514/18.8 |

FOREIGN PATENT DOCUMENTS

WO    2011/154402    12/2011

OTHER PUBLICATIONS

Sorrell et al. Journal of Cell Science 117, 667-675, 2004.*
Kalluri et al. Nature Reviews Cancer 6, pp. 392-401, May 2006.*
Yong Wang et al., "MicroRNA Regulation of Ionizing Radiation-Induced Premature Senescence", Int. J. Radiation Oncology Biol. Phys., vol. 81, No. 3, pp. 839-848, 2011.
Amel Boudjelal et al., "Compositional Analysis and In Vivo Anti-Diabetic Activity of Wild Algerian *Marrubium vulgare* L. Infusion", Elsevier, 2011, Fitoterapia 83 (2012) pp. 286-292.

* cited by examiner

*Primary Examiner* — Chris R Tate
*Assistant Examiner* — Douglas F White
(74) *Attorney, Agent, or Firm* — Young & Thompson

(57) ABSTRACT

Identification and use of compounds which inhibit the expression or activity of micro-RNAs for preventing and/or attenuating ageing. An in vitro method for screening for candidate compounds for preventing and/or attenuating ageing of the skin including (a) bringing at least one test compound in contact with a sample of fibroblasts, (b) measuring the expression or the activity of at least one microRNA chosen from miR-134 and miR-152 in said fibroblasts, and (c) selecting the compounds for which an inhibition of at least 20%, preferably at least 30%, preferably at least 40% of the expression or an inhibition of at least 20%, preferably at least 30%, preferably at least 40% of the activity of at least one microRNA is measured in the fibroblasts treated in (a) compared with the untreated fibroblasts.

12 Claims, 13 Drawing Sheets

Expression of miR-134 in fibroblasts is inhibited by the following compounds:

| Compound | Final concentration (%) | Renamed |
|---|---|---|
| Epigallocatechine Gallate | 0.01 | Compound 4.1 |
| Verbascoside | 0.001 | Compound 5.1 |

Treatment: 48 hrs

Expression of miR-152 in fibroblasts is inhibited by the following compounds:

| Compound | Final concentration (%) | Renamed |
|---|---|---|
| Catechine Hydrate | $2.10^{-4}$ | Compound 2.2 |
| Epigallocatechine Gallate | 0.01 | Compound 4.1 |
| Bois d'Ange PFA | $4.10^{-4}$ | Compound 8.2 |

Treatment: 48 hrs

INHIBITORS OF MICRO-RNAS FOR USE FOR PREVENTING AND/OR ATTENUATING SKIN AGEING

BACKGROUND OF THE INVENTION

Cellular senescence is a form of irreversible growth arrest, originally described for end-stage proliferative cells in culture, but known to be induced by several stimuli such as DNA damage, oxidative stress, chemotherapy and excess of mitotic stimuli such as oncogenic activation (Serrano et al 1997; Campisi 2001; Schmitt et al 2002). Cells enter in a stage of irreversible arrest, showing distinctive features, including enhanced beta-galactosidase activity and increased expression of key mediators including p53, promyelocitic leukemia protein (PML), p16INK4a and p19Arf (Serrano et al 1997; Narita et al 2003; Sharpless et al 2004). Although mostly studied in vitro, cellular senescence has been correlatively linked to the aging process at the level of the whole animal, thus implicating many of the factors that regulate senescence as contributing to organism aging (Sharpless and DePinho 2004, Campisi 2005).

All senescing cells undergo profound changes in gene expression. Comprehensive gene expression profiling has identified genes in cell cycle, insulin growth factor, interferon, MAP kinase and oxidative stress pathways as consistently dysregulated during cell senescence. Altered gene expression gives rise to the senescent phenotype, and is well established as part of the mechanisms and pathways that activate the senescence program in cells. However, the factors responsible for the alterations of gene expression during senescence remain elusive.

MicroRNAs (miRNAs) are key modulators of gene expression in various biological and pathological processes. Changes in miRNA expression levels occur in cellular senescence and organism aging (Grillari et al 2010; Hackl et al 2010), and have been linked to changes in levels of mRNAs that are putative targets of specific miRNAs (Lafferty et al 2009; He et al 2007; Maes et al 2009). Several studies have identified specific sets of miRNAs up-regulated in fibroblasts replicative senescence (Faraonio et al, 2012; Dhahbi et al, 2011; Yong Wang et al, 2010).

It is thus desirable and important to provide products or active agents which prevent, reduce or even inhibit the cellular senescence, particularly the fibroblast senescence.

The present invention thus provides a method for identifying such useful agents.

SUMMARY OF THE INVENTION

The present invention thus relates to an in vitro method for screening for candidate compounds for preventing and/or attenuating ageing of the skin, comprising the following steps:
a. bringing at least one test compound into contact with a sample of fibroblasts;
b. measuring the expression or the activity of at least one microRNA chosen from miR-134 and miR-152 in said fibroblasts;
c. selecting the compounds for which an inhibition of at least 20%, preferably at least 30%, preferably at least 40% of the expression or an inhibition of at least 20%, preferably at least 30%, preferably at least 40% of the activity of at least one microRNA is measured in the fibroblasts treated in a. compared with the untreated fibroblasts.

DETAILED DESCRIPTION OF THE INVENTION

Preferably, the fibroblasts are pre-senescent fibroblasts. Thus, the present invention relates to an in vitro method for screening for candidate compounds for preventing and/or attenuating ageing of the skin, comprising the following steps:
a. bringing at least one test compound into contact with a sample of pre-senescent fibroblasts;
b. measuring the expression or the activity of at least one microRNA chosen from miR-134 and miR-152 in said pre-senescent fibroblasts;
c. selecting the compounds for which an inhibition of at least 20%, preferably at least 30%, preferably at least 40% of the expression or an inhibition of at least 20%, preferably at least 30%, preferably at least 40% of the activity of at least one microRNA is measured in the pre-senescent fibroblasts treated in a. compared with the untreated pre-senescent fibroblasts.

By "pre-senescent fibroblasts", it is meant cells which express p16 at a detectable level (this level can be determined by Western blot). These cells proliferate slower than young fibroblasts.

According to a first embodiment, step b. is performed before and after step a. In this case, the expression or activity of the microRNA (chosen from miR-134 and miR-152) measured in the fibroblasts, preferably pre-senescent, before step a. corresponds to the control value (i.e. untreated fibroblasts, preferably pre-senescent). Thus, step c. comprises the selection of the compounds for which an inhibition of at least 20%, preferably at least 30%, preferably at least 40% of the expression or an inhibition of at least 20%, preferably at least 30%, preferably at least 40% of the activity of at least one microRNA is measured in the fibroblasts, preferably pre-senescent, treated in a. compared with the same fibroblasts, preferably pre-senescent, before step a.

According to another embodiment, the method comprises a first step a'. of preparing samples of fibroblasts, preferably pre-senescent. Thus, preferably, the present invention relates to an in vitro method for screening for candidate compounds for preventing and/or attenuating ageing of the skin, comprising the following steps:
a'. preparing at least two samples of fibroblasts, preferably pre-senescent;
a. bringing one of the samples into contact with at least one test compound; then
b. measuring the expression or the activity of at least one microRNA chosen from miR-134 and miR-152 in said samples; and
c. selecting the compounds for which an inhibition of at least 20%, preferably at least 30%, preferably at least 40% of the expression or an inhibition of at least 20%, preferably at least 30%, preferably at least 40% of the activity of at least one microRNA is measured in the fibroblasts, preferably pre-senescent, treated in a. compared with the sample of untreated fibroblasts, preferably pre-senescent.

In this second embodiment, the expression or activity of the microRNA chosen from miR-134 and miR-152 measured in the sample of fibroblasts, preferably pre-senescent, and not submitted to step a., corresponds to the control value (i.e. untreated fibroblasts, preferably pre-senescent).

By the expression "ageing of the skin" is intended any change in the external appearance of the skin due to ageing, whether this is chronobiological and/or photo-induced, such as, for example, wrinkles and fine lines, withered skin, flaccid skin, thinned skin, and skin lacking elasticity and/or tonus, and also any internal change in the skin which is not systematically reflected by a changed external appearance, such as, for example, any internal degradation of the skin, particularly of collagen, following exposure to ultraviolet radiation.

The miRs of interest according to the invention are chosen from miR-134 and miR-152.

Mature miR-134 is of SEQ ID No. 1 (ugugacugguugacca-gagggg). It is the sequence HGNC:31519;

Mature miR-152 is of SEQ ID No. 2 (UCAGUG-CAUGACAGAACUUGG). It is the sequence HGNC: 31538.

These sequences come from the HGNC database.

MiR-134 function is unknown, while miR-152 as been described as tumour suppressor in endometrial cancer (Tsuruta et al, 2011) and in hepatocellular carcinomas (Huang et al, 2010), in the latter it targets the DNA methyltransferase 1, causing aberrant DNA methylation. Without being bound by any theory, the examples show that both miRNAs have as targets the integrin alpha 9 (ITGA9), while miR-152 targets ITGA5. Integrins are heterodimeric integral membrane glycoproteins composed of an alpha chain and a beta chain that mediate cell-cell and cell-matrix adhesion. The protein encoded by ITGA9, when bound to the beta 1 chain, forms an integrin that is a receptor for VCAM1, cytotactin, osteopontin and fibronectin-EIIIA (FN-EIIIA, also called EDA) in the extracellular matrix. In general, cell-matrix adhesion receptors such as integrins play essential roles in developmental processes that involve close interactions between the cells and their surrounding extracellular matrix (ECM). In addition to mediating attachment to their respective ECM ligand(s), integrins have specialized signaling functions and they can regulate gene expression as well as cell shape, migration, proliferation, and survival. Furthermore, integrin binding to ECM is not only required for transducing signals from the matrix to cells, but this interaction also initiates responses that allow the cells to organize and remodel the matrix (Leiss et al, 2008); this feature is very limited in aged tissues and in particular in aged skin. Recent studies have shown that α9β1 integrin (ITAG9) increase the expression of matrix-degrading proteases (Roy et al, 2011), which degrade collagen and other extracellular matrix proteins that comprise the dermal connective tissue during aging (Quan et al, 2009).

The test compounds tested may be of any type. They may be of natural origin or may have been produced by chemical synthesis. This may involve a library of structurally defined chemical compounds, uncharacterized compounds or substances, or a mixture of compounds.

Natural compounds include compounds from vegetal origin, like plants and animals. Preferably, the test compounds are vegetal, preferably chosen from botanical extracts.

The pre-senescent fibroblasts used in steps a'. and a. above are a cellular model for replicative senescence. These pre-senescent fibroblasts are obtained after 70 population doublings in classical culture conditions. The classical culture conditions comprise a culture of the fibroblasts in 106 medium added with LSGS growth supplements, constantly kept in a subconfluent state.

Preferably, they are obtained thanks to the following process:

Neonatal Human Primary Dermal Fibroblasts are cultured in an appropriate medium. Said medium may be 106 medium added with LSGS growth supplements. They are constantly kept subconfluent. Cells are passaged at appropriate periods of time, usually once a week.

At each passage, a portion of the cells is collected and analyzed to measure population doublings, population doubling time, senescence biochemical markers and cell cycle.

Preferably, the population doublings of primary human fibroblasts is measured during around 100 days of culture. Analysis of senescent marker (p16) suggests that while the proliferation marker (p1) decreases, the cells are not differentiating. The percentage of proliferating cells is diminishing during senescence.

According to step a., the test compound is put into contact with a sample of fibroblasts, preferably pre-senescent.

According to step b., the expression and/or the activity of at least one microRNA chosen from miR-134 and miR-152 is measured in said fibroblasts, preferably pre-senescent.

The term "expression of a microRNA" is intended to mean the amount of produced microRNA.

The term "activity of a microRNA" is intended to mean the ability of said microRNA to inhibit the level of the mRNA to which it hybridizes.

Those skilled in the art are familiar with the techniques for quantitatively or semi-quantitatively detecting the mRNA to which said microRNA hybridizes, and thus, determining said microRNA activity. Techniques based on hybridization of the mRNA with specific nucleotide probes are the most common, like Northern blotting, RT-PCR (reverse transcriptase polymerase chain reaction), quantitative RT-PCR (qRT-PCR).

Those skilled in the art are also familiar with the techniques for quantitatively or semi-quantitatively detecting the microRNA, or the mRNA to which said microRNA hybridizes. In particular, the expression of the microRNA can be measured by real-time PCR. The activity of the microRNA can be measured by real-time PCR on the mRNA targets, or by evaluating the protein level of the target by Western blot. Alternatively, if the target is unknown, the activity of the microRNA can be tested by evaluating the biological effect of the microRNA itself, such as an effect on beta-gal staining or on proliferation.

Preferably, the expression of the microRNA is measured by real-time PCR.

The expression or activity of the microRNA after treatment with the test compound is then compared to a control value, i.e. a value obtained in the same fibroblasts (preferably pre-senescent) before treatment, or a value obtained in another sample of fibroblasts (preferably pre-senescent) which are untreated.

According to step c., the useful compounds are those for which an inhibition of at least 20%, preferably at least 30%, preferably at least 40% of the expression or an inhibition of at least 20%, preferably at least 30%, preferably at least 40% of the activity of at least one microRNA is measured in the treated fibroblasts, preferably pre-senescent, compared with untreated fibroblasts, preferably pre-senescent. Preferably, the inhibition of the expression or of the activity of said microRNA is of at least 50%, preferably of at least 60%.

The compounds selected by means of the screening methods defined herein can subsequently be tested on other in vitro models and/or in vivo models for their effects on skin ageing. The useful compounds according to the invention are inhibitors of the targeted microRNA, i.e. chosen from miR-134 and miR-152.

A subject of the invention is also the cosmetic use of an inhibitor of at least one microRNA chosen from miR-134 and miR-152, said inhibitor being identified according to the above described method, for preventing and/or attenuating ageing of the skin.

According to another aspect, an objet of the present invention is the use of at least one microRNA inhibitor, said inhibitor being identified according to the above described method, to make a therapeutic composition for preventing and/or attenuating ageing of the skin. The present invention thus also relates to the use of at least one microRNA inhibitor, said inhibitor being identified according to the above described method, for preventing and/or attenuating ageing of the skin.

The inhibitor refers to a compound which eliminates or substantially reduces the expression or activity of the microRNA chosen from miR-134 and miR-152. The term "substantially" signifies a reduction of at least 20%, preferably at least 30%, preferably at least 40%, preferably of at least 50%, and more preferably of at least 60%.

The microRNA inhibitor can be used in a proportion of from 0.001 to 10% by weight, preferably in a proportion of from 0.01 to 5% by weight of the composition.

The inhibitor may be an antisense DNA or RNA polynucleotide or a siRNA. Preferably, inhibitors of microRNA (miR) are anti-miRs.

Anti-miRs are miR inhibitors that specifically inhibit endogenous miRs. Anti-miRs are single stranded nucleic acids designed to specifically bind to and inhibit endogenous microRNA molecules. Anti-miRs have nucleic sequence complementary to the sequence of the target miR. These ready-to-use inhibitors can be introduced into cells using transfection or electroporation parameters similar to those used for siRNAs, and enable detailed study of miR biological effects. Use of the anti-miR enables miR functional analysis by down-regulation of miR activity.

Anti-miRs are commercially available; they can for example be obtained by Ambion or Applied Biosystems.

Based on literature, it is possible that 70% inhibition of miR expression will have an effect on induction/inhibition of senescence in human normal cells (Menghini R, Casagrande V, Cardellini M, Martelli E, Terrinoni A, Amati F, Vasa-Nicotera M, Ippoliti A, Novelli G, Melino G, Lauro R, Federici M., MicroRNA 217 modulates endothelial cell senescence via silent information regulator 1. Circulation. 2009; 120(15):1524-32).

The miR inhibitors identified thanks to the screening method described above can be formulated within a composition, in combination with a physiologically acceptable carrier, preferably a cosmetically acceptable medium, i.e. a medium that is suitable for use in contact with human skin without any risk of toxicity, incompatibility, instability or allergic response and especially that does not cause any sensations of discomfort (redness, tautness, stinging, etc.) that are unacceptable to the user. These compositions may be administered, for example, orally, or topically. Preferably, the composition is applied topically. By oral administration, the composition may be in the form of tablets, gel capsules, sugar-coated tablets, syrups, suspensions, solutions, powders, granules, emulsions, suspensions of microspheres or nanospheres or lipid or polymeric vesicles for controlled release. By topical administration, the composition is more particularly for use in treating the skin and the mucous membranes and may be in the form of salves, creams, milks, ointments, powders, impregnated pads, solutions, gels, sprays, lotions or suspensions. It may also be in the form of suspensions of microspheres or nanospheres or lipid or polymeric vesicles or polymeric patches or hydrogels for controlled release. This composition for topical application may be in anhydrous form, in aqueous form or in the form of an emulsion. The composition for topical application may be in the form of an oil-in-water, water-in-oil or multiple emulsion (W/O/W or O/W/O), which may optionally be microemulsions or nanoemulsions, or in the form of an aqueous dispersion, a solution, an aqueous gel or a powder. In a preferred variant, the composition is in the form of a gel, a cream or a lotion.

The physiologically acceptable carrier of the composition generally comprises water and optionally other solvents such as ethanol.

This composition is preferably used as a care and/or cleansing product for facial and/or bodily skin and it may especially be in the form of a fluid, a gel or a mousse, conditioned, for example, in a pump-dispenser bottle, an aerosol or a tube, or in the form of cream conditioned, for example, in a jar. As a variant, it may be in the form of a makeup product and in particular a foundation or a loose or compact powder.

It may comprise various adjuvants, such as at least one compound chosen from:
  oils, which may be chosen especially from: linear or cyclic, volatile or non-volatile silicone oils, such as polydimethylsiloxanes (dimethicones), polyalkylcyclosiloxanes (cyclomethicones) and polyalkylphenylsiloxanes (phenyl dimethicones); synthetic oils such as fluoro oils, alkylbenzoates and branched hydrocarbons such as polyisobutylene; plant oils and especially soybean oil or jojoba oil; and mineral oils such as liquid petroleum jelly;
  waxes such as ozokerite, polyethylene wax, beeswax or carnauba wax;
  silicone elastomers obtained especially by reaction, in the presence of a catalyst, of a polysiloxane containing at least one reactive group (especially hydrogen or vinyl) and bearing at least one alkyl group (especially methyl) or phenyl, in a terminal and/or side position, with an organosilicone such as an organohydrogenopolysiloxane;
  surfactants, preferably emulsifying surfactants, whether they are nonionic, anionic, cationic or amphoteric, and in particular fatty acid esters of polyols such as fatty acid esters of glycerol, fatty acid esters of sorbitan, fatty acid esters of polyethylene glycol and fatty acid esters of sucrose; fatty alkyl ethers of polyethylene glycol; alkylpolyglucosides; polysiloxane-modified polyethers; betaine and derivatives thereof; polyquaterniums; ethoxylated fatty alkyl sulfate salts; sulfosuccinates; sarcosinates; alkyl and dialkyl phosphates, and salts thereof; and fatty acid soaps;
  co-surfactants such as linear fatty alcohols and in particular cetyl alcohol and stearyl alcohol;
  thickeners and/or gelling agents, and in particular cross-linked or non-crosslinked, hydrophilic or amphiphilic homopolymers and copolymers, of acryloylmethylpropanesulfonic acid (AMPS) and/or of acrylamide and/or of acrylic acid and/or of acrylic acid salts or esters; xanthan gum or guar gum; cellulose derivatives; and silicone gums (dimethiconol);
  organic screening agents, such as dibenzoylmethane derivatives (including butylmethoxydibenzoylmethane), cinnamic acid derivatives (including ethylhexyl methoxycinnamate), salicylates, para-aminobenzoic acids, β,β'-diphenyl acrylates, benzophenones, benzylidenecamphor derivatives, phenylbenzimidazoles, triazines, phenylbenzotriazoles and anthranilic derivatives;

inorganic screening agents, based on mineral oxides in the form of coated or uncoated pigments or nanopigments, and in particular based on titanium dioxide or zinc oxide;

dyes;

preserving agents;

sequestrants such as EDTA salts;

fragrances;

and mixtures thereof, without this list being limiting.

Examples of such adjuvants are especially mentioned in the CTFA dictionary (International Cosmetic Ingredient Dictionary and Handbook published by The Cosmetic, Toiletry and Fragrance Association, 11th edition, 2006), which describes a wide variety, without limitation, of cosmetic and pharmaceutical ingredients usually used in the skincare industry, that are suitable for use as additional ingredients in the compositions according to the present invention.

The composition may also comprise at least one compound with an optical effect such as fillers, pigments, nacres, tensioning agents and matting polymers, and mixtures thereof.

The term "fillers" should be understood as meaning colorless or white, mineral or synthetic, lamellar or non-lamellar particles suitable for giving the composition body or rigidity and/or softness, a matt effect and uniformity immediately on application. Fillers that may especially be mentioned include talc, mica, silica, kaolin, Nylon® powders such as Nylon-12 (Orgasol® sold by the company Atochem), polyethylene powders, polyurethane powders, polystyrene powders, polyester powders, optionally modified starch, silicone resin microbeads such as those sold by the company Toshiba under the name Tospearl®, hydroxyapatite, and hollow silica microspheres (Silica Beads® from the company Maprecos).

The term "pigments" should be understood as meaning white or colored, mineral or organic particles that are insoluble in the medium, which are intended to color and/or opacify the composition. They may be of standard or nanometric size. Among the mineral pigments that may be mentioned are titanium dioxide, zirconium dioxide and cerium dioxide, and also zinc oxide, iron oxide and chromium oxide.

The term "nacres" should be understood as meaning iridescent particles that reflect light. Among the nacres that may be envisaged, mention may be made of natural mother-of-pearl, mica coated with titanium oxide, with iron oxide, with natural pigment or with bismuth oxychloride, and also colored titanium mica.

The mass concentration in the aqueous phase of these fillers and/or pigments and/or nacres is generally from 0.1% to 20% and preferably from 0.2% to 7% by weight relative to the total weight of the composition.

The term "tensioning agent" should be understood as meaning a compound suitable for making the skin taut and, by means of this tension effect, making the skin smooth and reducing or even immediately eliminating wrinkles and fine lines therefrom. Tensioning agents that may be mentioned include polymers of natural origin. The term "polymer of natural origin" means polymers of plant origin, polymers derived from integuments, egg proteins and latices of natural origin. These polymers are preferably hydrophilic. Polymers of plant origin that may especially be mentioned include proteins and protein hydrolyzates, and more particularly extracts of cereals, of legumes and of oil-yielding plants, such as extracts of corn, of rye, of wheat, of buckwheat, of sesame, of spelt, of pea, of bean, of lentil, of soybean and of lupin. The synthetic polymers are generally in the form of a latex or a pseudolatex and may be of polycondensate type or obtained by free-radical polymerization. Mention may be made especially of polyester/polyurethane and polyether/polyurethane dispersions. Preferably, the tensioning agent is a copolymer of PVP/dimethiconyl acrylate and of hydrophilic polyurethane (Aquamere S-2001® from the company Hydromer).

The term "matting polymers" means herein any polymer in solution, in dispersion or in the form of particles, which reduces the sheen of the skin and which unifies the complexion. Examples that may be mentioned include silicone elastomers; resin particles; and mixtures thereof. Examples of silicone elastomers that may be mentioned include the products sold under the name KSG® by the company Shin-Etsu, under the name Trefil®, BY29® or EPSX® by the company Dow Corning or under the name Gransil® by the company Grant Industries.

The composition used according to the invention may also comprise active agents other than the micro-RNA inhibitor, and in particular at least one active agent chosen from: agents that stimulate the production of growth factors; anti-glycation or deglycating agents; agents that increase collagen synthesis or that prevent its degradation (anti-collagenase agents and especially matrix metalloprotease inhibitors); agents that increase elastin synthesis or prevent its degradation (anti-elastase agents); agents that stimulate the synthesis of integrin or of focal adhesion constituents such as tensin; agents that increase the synthesis of glycosaminoglycans or proteoglycans or that prevent their degradation (anti-proteoglycanase agents); agents that increase fibroblast proliferation; depigmenting or anti-pigmenting agents; antioxidants or free-radical scavengers or anti-pollution agents; and mixtures thereof, without this list being limiting.

Examples of such agents are especially: plant extracts and in particular extracts of *Chondrus crispus*, of *Thermus thermophilus*, of *Pisum sativum* (Proteasyl® TP LS), of *Centella asiatica*, of *Scenedesmus*, of *Moringa pterygosperma*, of witch hazel, of *Castanea sativa*, of *Hibiscus sabdriffa*, of *Polianthes tuberosa*, of *Argania spinosa*, of *Aloe vera*, of *Narcissus tarzetta*, or of liquorice; an essential oil of *Citrus aurantium* (Neroli); α-hydroxy acids such as glycolic acid, lactic acid and citric acid, and esters thereof; β-hydroxy acids such as salicylic acid and derivatives thereof; plant protein hydrolyzates (especially of soybean or of hazelnut); acylated oligopeptides (sold especially by the company Sederma under the trade names Maxilip®, Matrixyl® 3000, Biopeptide® CL or Biopeptide® EL); yeast extracts and in particular of *Saccharomyces cerevisiae*; algal extracts and in particular of laminairia; vitamins and derivatives thereof such as retinyl palmitate, ascorbic acid, ascorbyl glucoside, magnesium or sodium ascorbyl phosphate, ascorbyl palmitate, ascorbyl tetraisopalmitate, ascorbyl sorbate, tocopherol, tocopheryl acetate and tocopheryl sorbate; arbutin; kojic acid; ellagic acid; and mixtures thereof.

As a variant or in addition, the composition used according to the invention may comprise at least one elastase inhibitor (anti-elastase), such as an extract of *Pisum sativum* seeds that is sold especially by the company Laboratoires Sérobiologiques/Cognis France under the trade name Proteasyl TP LS®.

The composition may also contain inert additives or combinations of these additives, such as wetting agents, stabilizers, moisture regulators, pH regulators, osmotic pressure modifiers, or UV-A and UV-B screens.

BRIEF DESCRIPTION OF THE DRAWINGS

The following examples illustrate the invention without limiting the scope thereof. These examples are based on the figures listed below.

(A) Population doublings of primary human fibroblasts during 103 days of culture. After 70 population doublings the growth curve has a plateau, showing that cells stop dividing and are reaching the senescent state. (B) Western blots performed on protein extracts from human fibroblasts at passage 1(p1), p4, p8 and p16 showing the analysis of some senescence markers, such as sirt1 and p16. β-Actin was used as loading control. (C) Human fibroblasts at p1, p4, p8 and p16 were subjected to a 3 h BrdU pulse, collected, propidium iodide (PI)-stained, and analyzed by flow cytometry. BrdU-positive cells are indicated as S-phase fluorescent population and are assesd by PI staining of DNA content of 2n or 4n (fixed to values of 250 and 400 in the plots). (D and E) SA-β-galactosidase staining and quantification by blue-cell/field of fibroblasts at p1, p4, p8 and p12.

Figure 2:
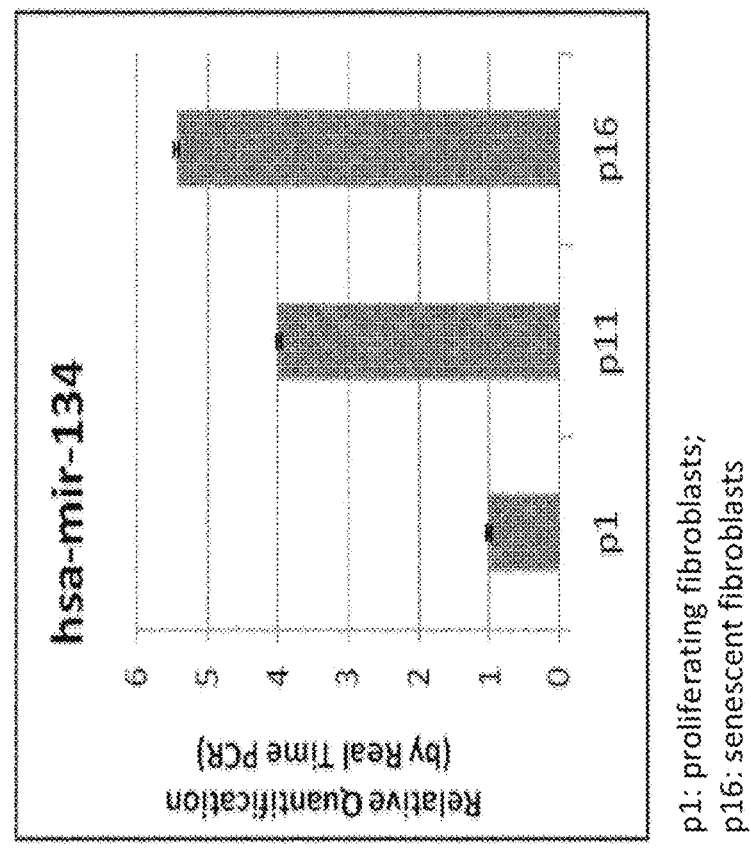

FIG. 2
Expression of miR-134 in Fibroblasts Replicative Senescence.

Relative quantification by Real Time PCR of miR-134 was performed on total RNAs collected from proliferating p1, pre-senescent p11 and senescent p16 fibroblasts.

Figure 3:
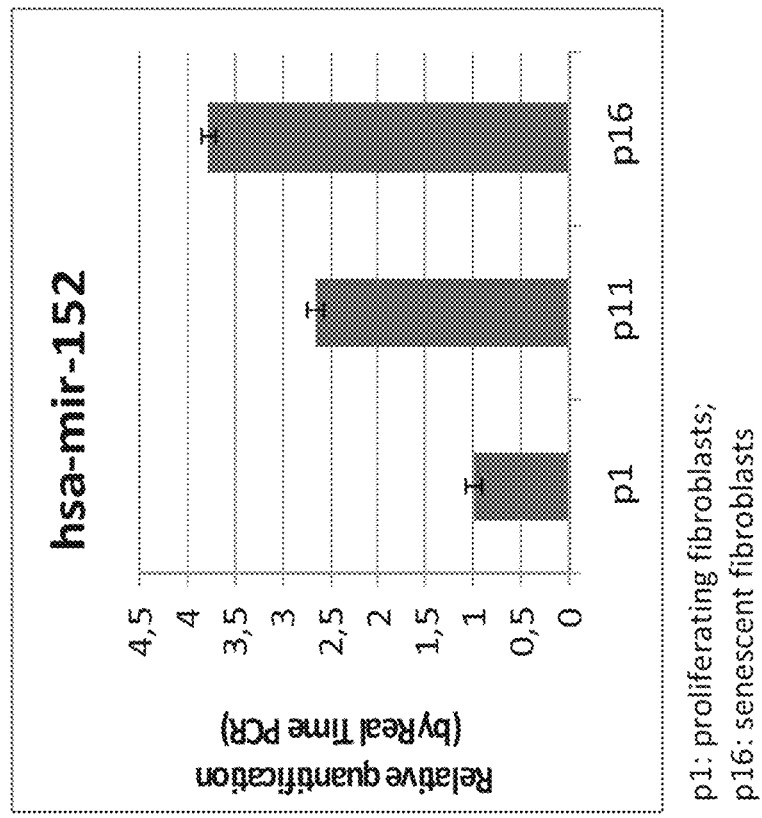

FIG. 3
Expression of miR-152 in Fibroblasts Replicative Senescence.

Relative quantification by Real Time PCR of miR-134 was performed on total RNAs collected from proliferating p1, pre-senescent p11 and senescent p16 fibroblasts.

Figure 4:
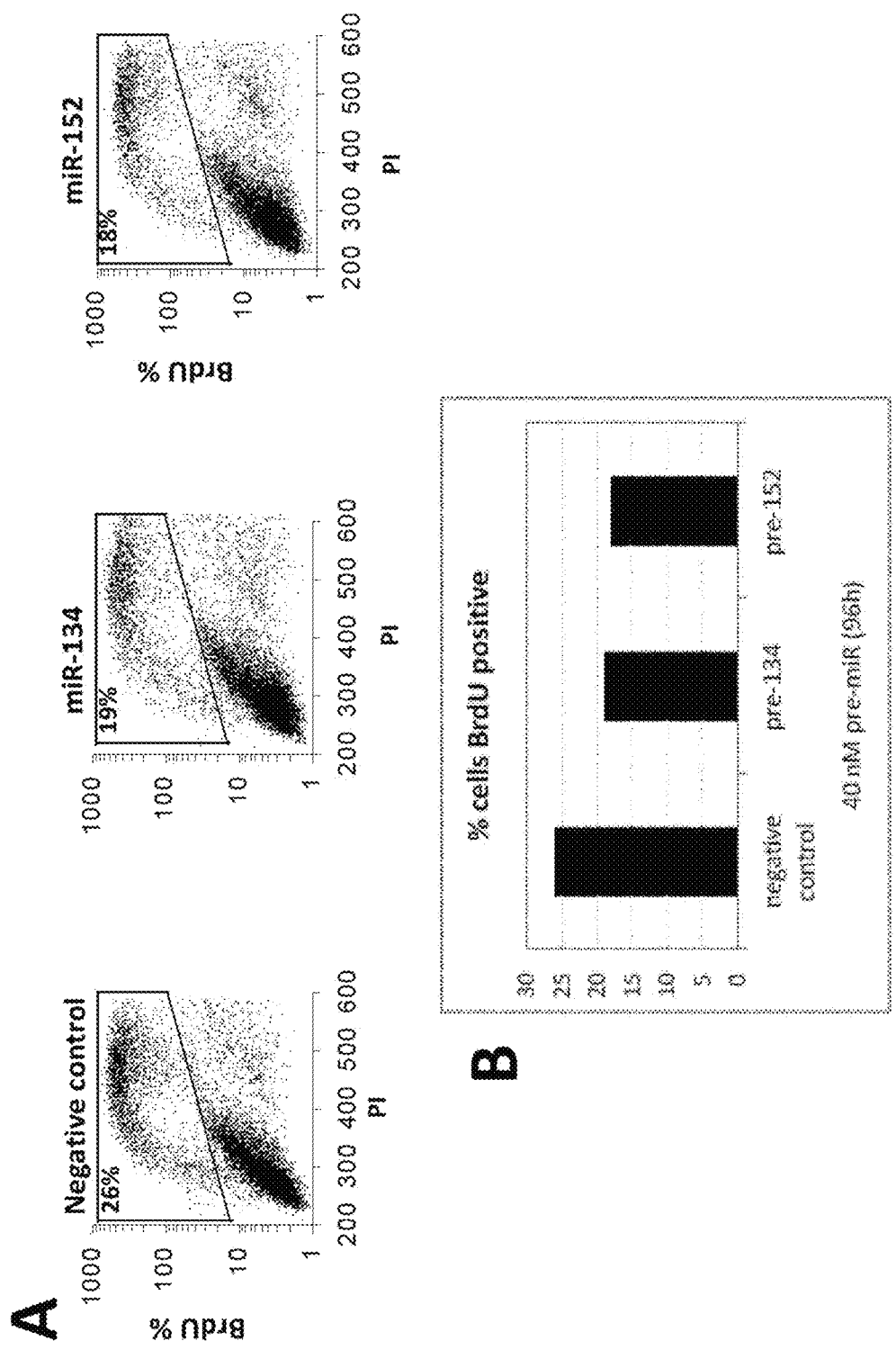

FIG. 4
MiR-134 and miR-152 Reduce Proliferation in Fibroblasts Upon Transfection in Proliferating/Young Fibroblasts.

Figure 1:
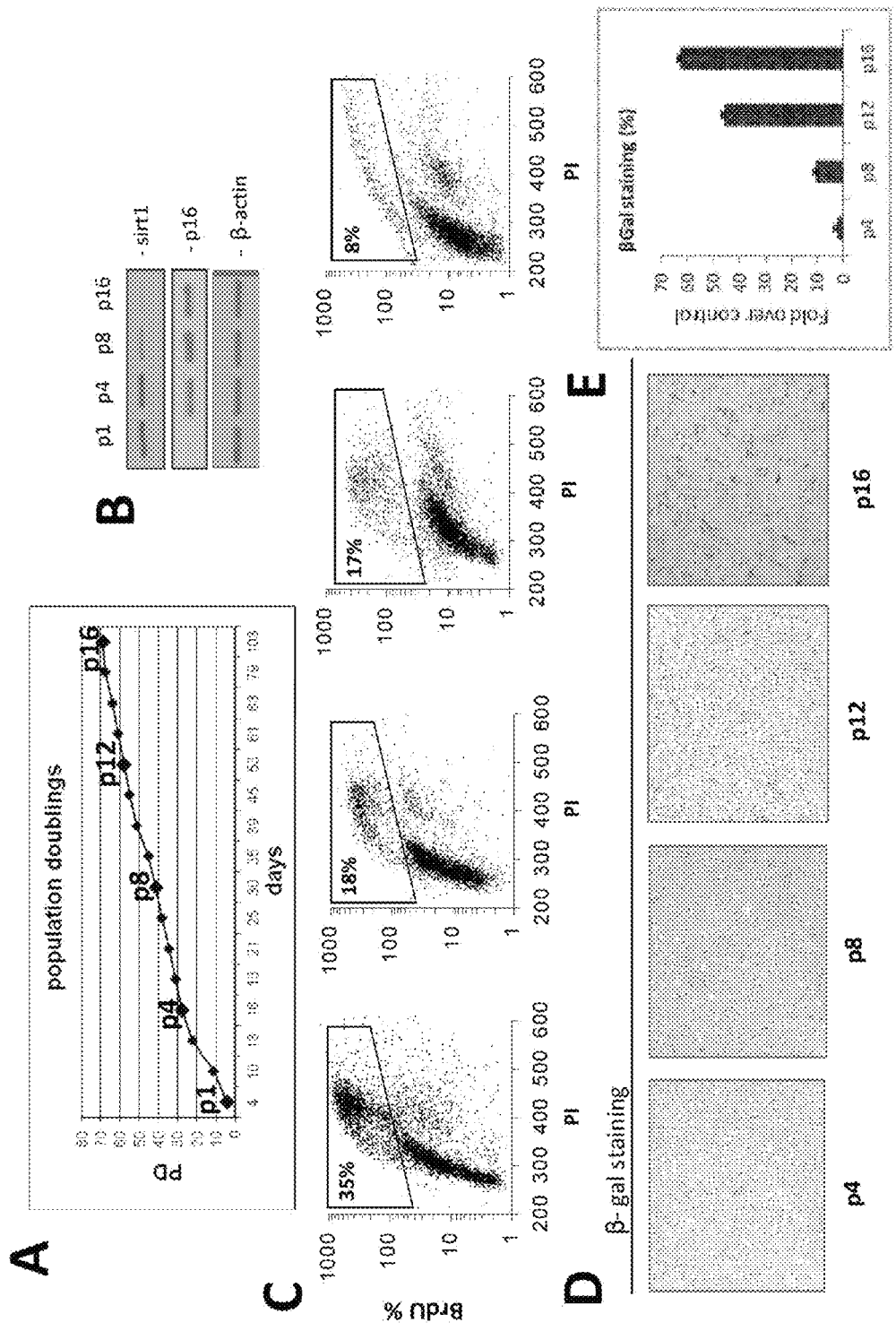
FIG. 1
Induction of Replicative Senescence in Human Dermal Fibroblasts.

(A) Ninety-six hours after transfection of fibroblasts with a negative control, miR-134 or miR-152 sequences, cells were subjected to a 3 h BrdU pulse, collected, PI-stained, and analyzed by flow cytometry as described in FIG. 1. (B) Quantification of BrdU positive fibroblasts after transfecion with negative control, miR-134 and miR-152 sequences.

Figure 5:
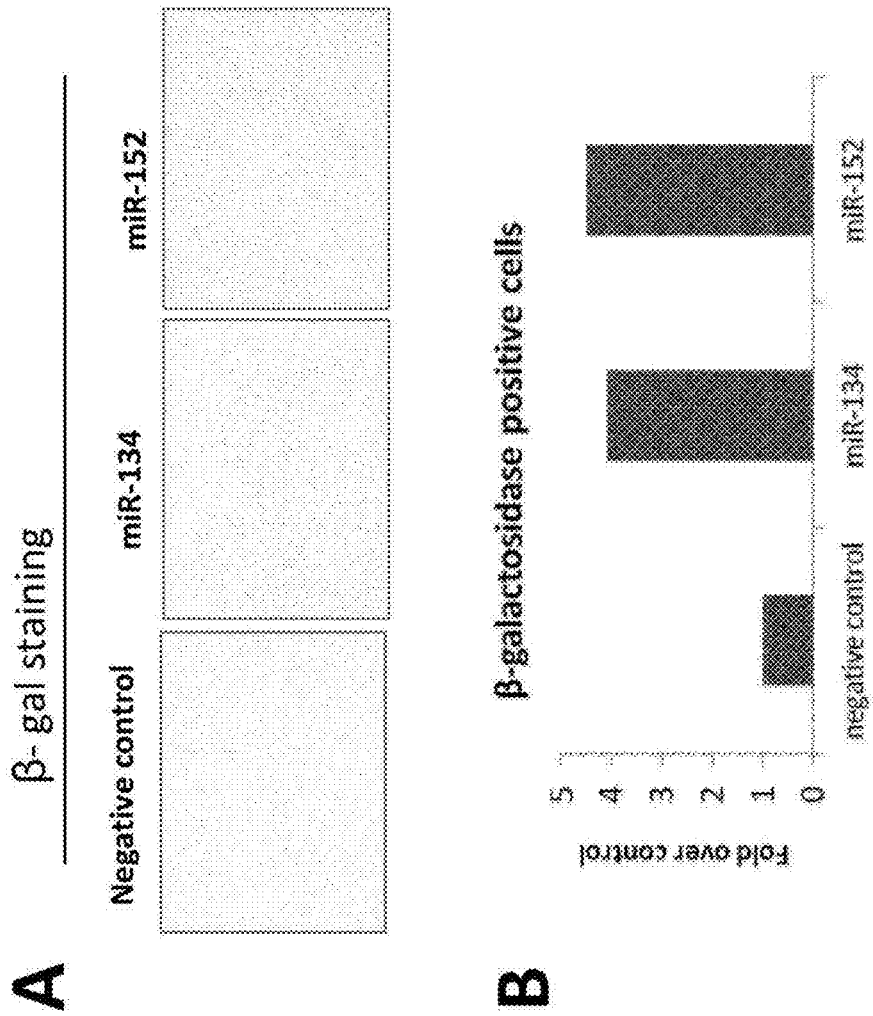

FIG. 5
MiR-134 and miR-152 Induce Senescence in Fibroblasts Upon Transfection in Proliferating/Young Fibroblasts.

(A and B) SA-β-galactosidase staining and quantification by blue-cell/field of fibroblasts ninety-six hours after transfection with negative control, miR-134 and miR-152 sequences.

Figure 6:
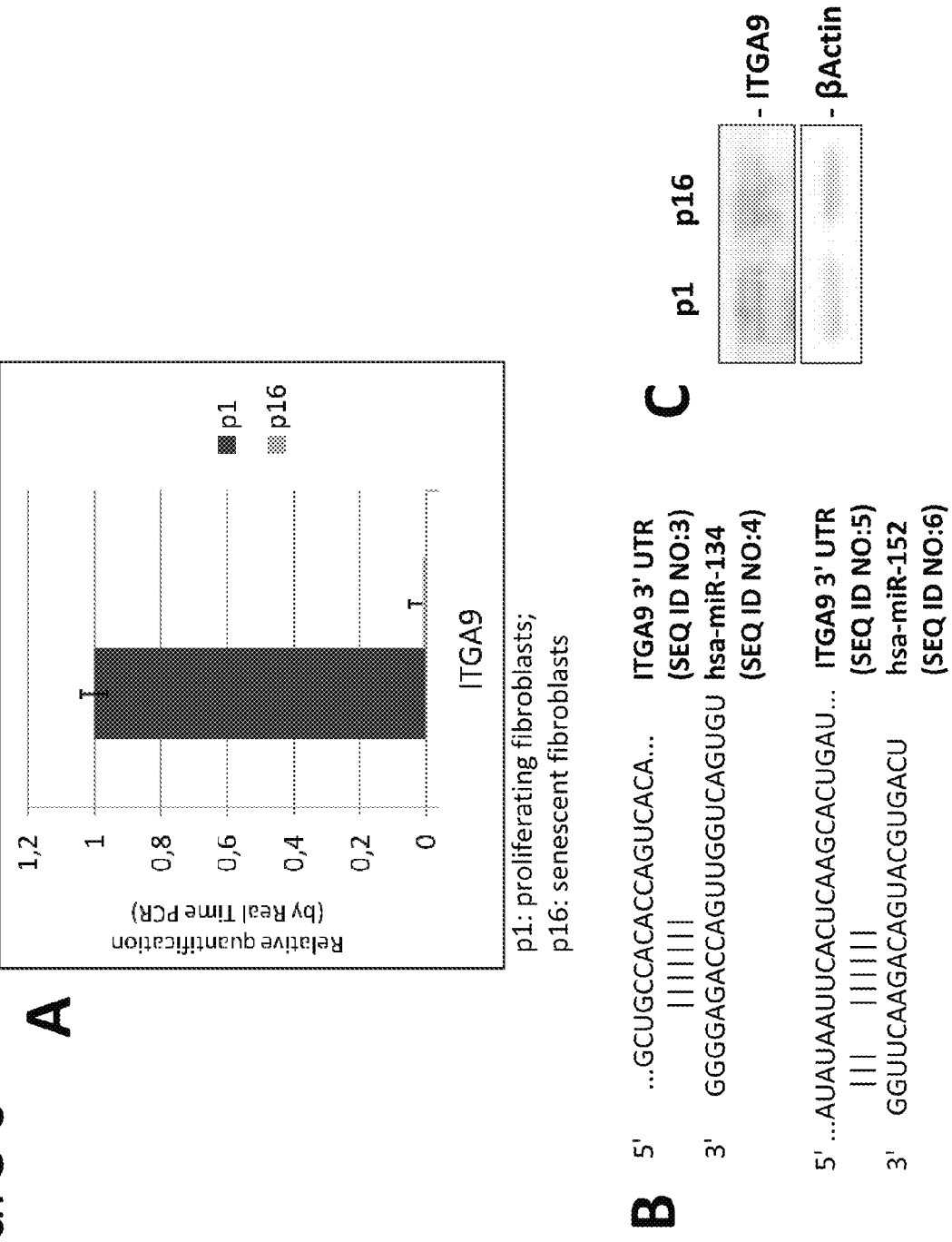

FIG. 6
ITGA9 is a Putative Target of miR-134 and miR-152 and Decreases in Fibroblast Replicative Senescence.

(A) Relative quantification by Real Time PCR of ITGA9 mRNA level at p1 and p16. (B) Predicted miR-134 and miR-152 target sites on ITGA9 3'UTR were identified by TargetScan 6.1 software. (C) Western blots performed on protein extracts from fibroblasts at p1 and p16 showing the protein level of ITGA9. β-Actin was used as loading control.

Figure 7:
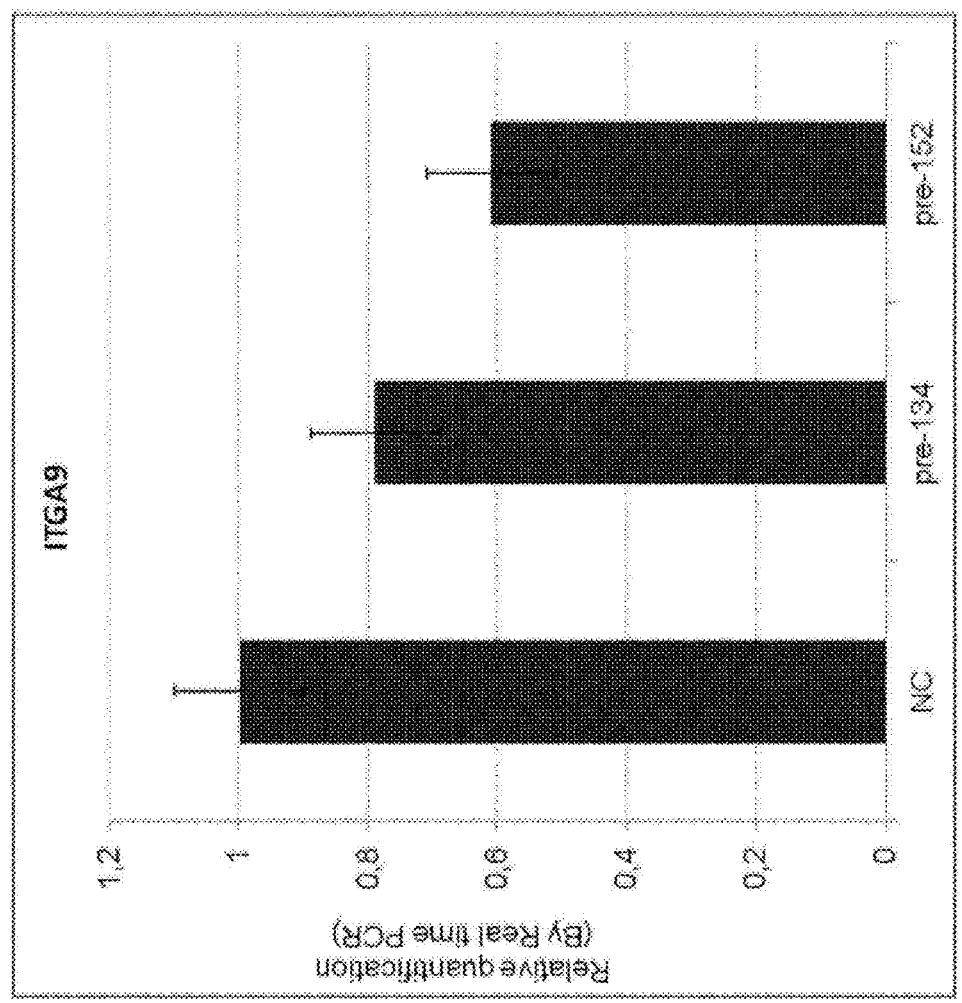

FIG. 7
ITGA9 mRNA is Downregulated Upon miR-134 and miR-152 Transfection in Fibroblasts.

Relative quantification by Real Time PCR of ITGA9 mRNA level of fibroblasts ninety-six hours after transfection with negative control, miR-134 and miR-152 sequences.

Figure 8:
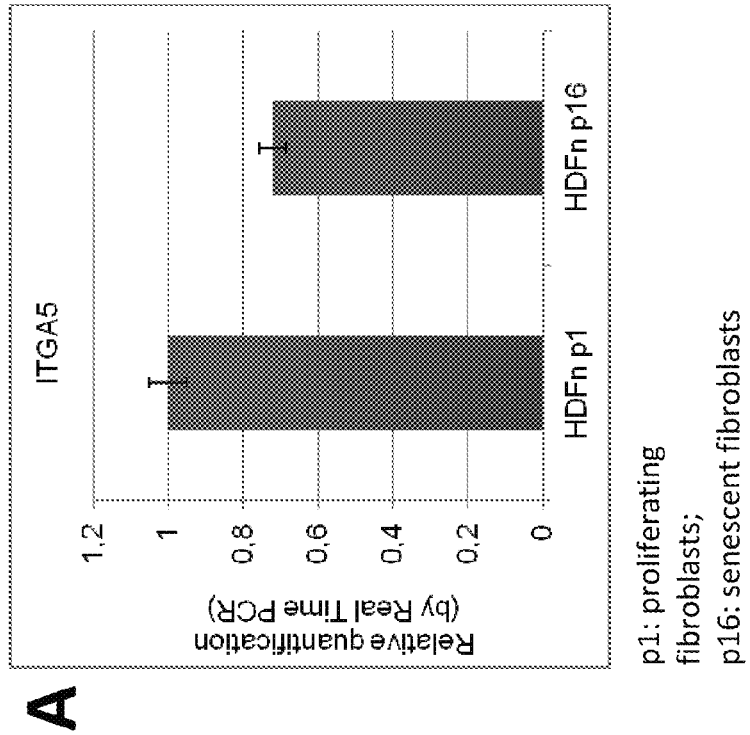
Figure 8:

FIG. 8
ITGA5 is a Putative Target of miR-152 and Decreases in Fibroblasts Replicative Senescence.

(A) Relative quantification by Real Time PCR of ITGA5 mRNA level at p1 and p16. (B) Predicted miR-152 target sites on ITGA 3'UTR were identified by TargetScan 6.1 software. (C) Western blots performed on protein extracts from fibroblasts at p1 and p16 showing the protein level of ITGA5. β-Actin was used as loading control.

Figure 9:
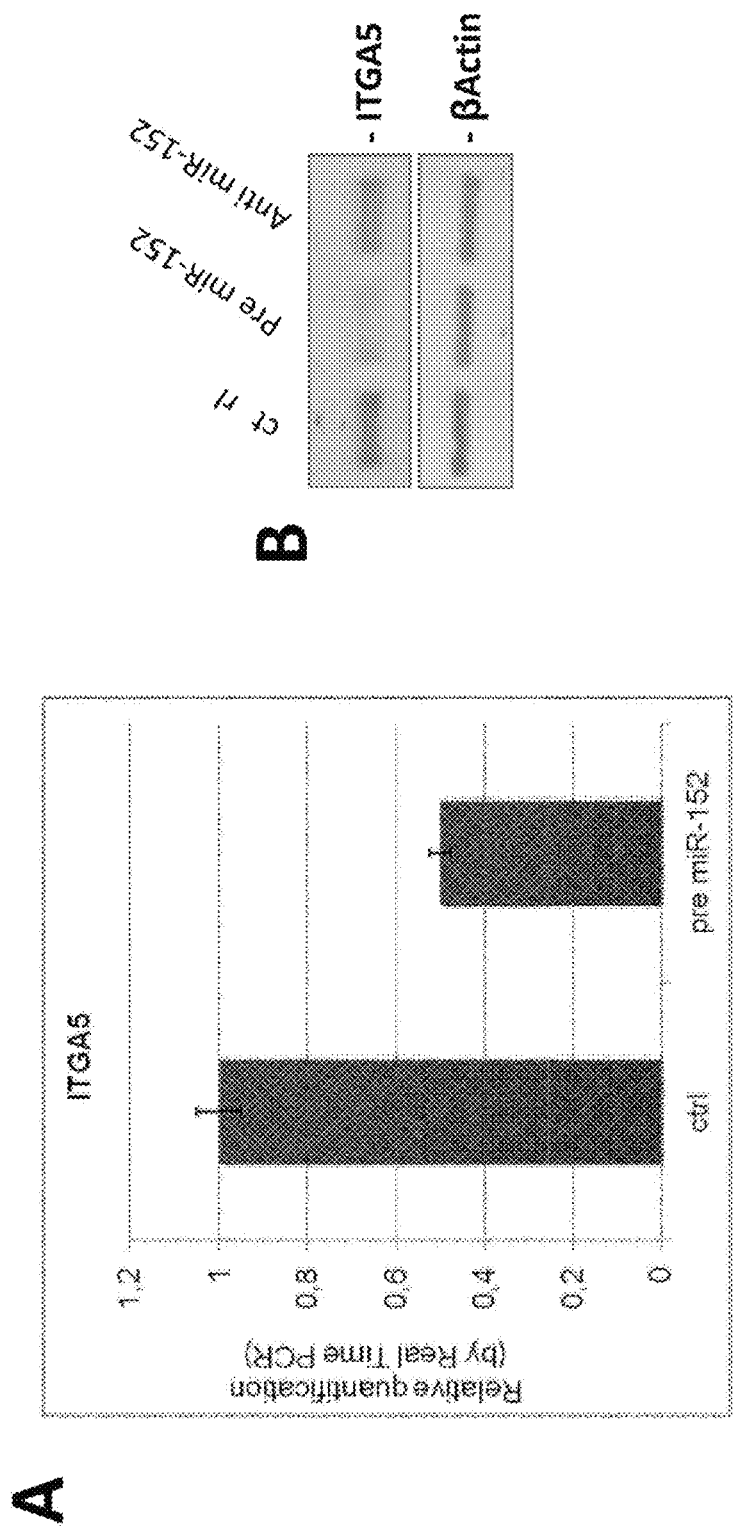

FIG. 9
ITGA5 is Downregulated Upon miR-152 Transfection in Fibroblasts.

(A) Relative quantification by Real Time PCR of ITGA5 mRNA level of fibroblasts ninety-six hours after transfection with negative control and miR-152 sequences. (B) Western blots performed on protein extracts from fibroblasts ninety-six hours after transfection with negative control, miR-152 and anti-miR 152 sequences showing the protein level of ITGA5. β-Actin was used as loading control.

Figure 10:
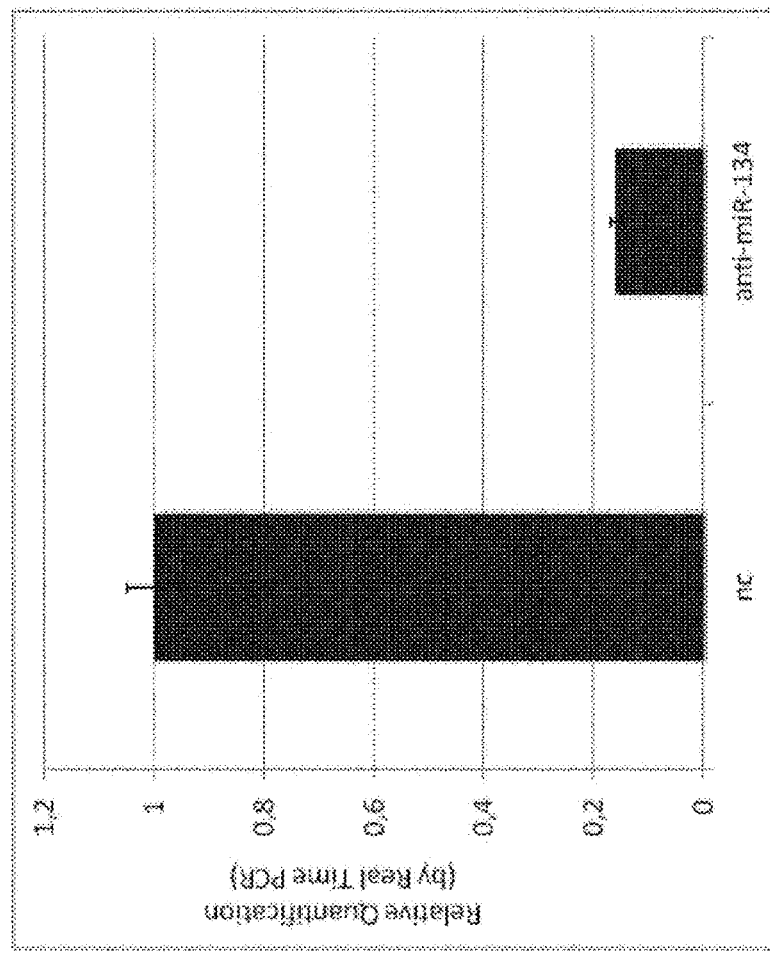

FIG. 10
Inhibition of miR-134 Using Specific AntagomiR in Fibroblasts.

Relative quantification by Real Time PCR of miR-134 level ninety-six hours after transfection of fibroblasts with negative control and anti-miR-134 sequences.

Figure 11:
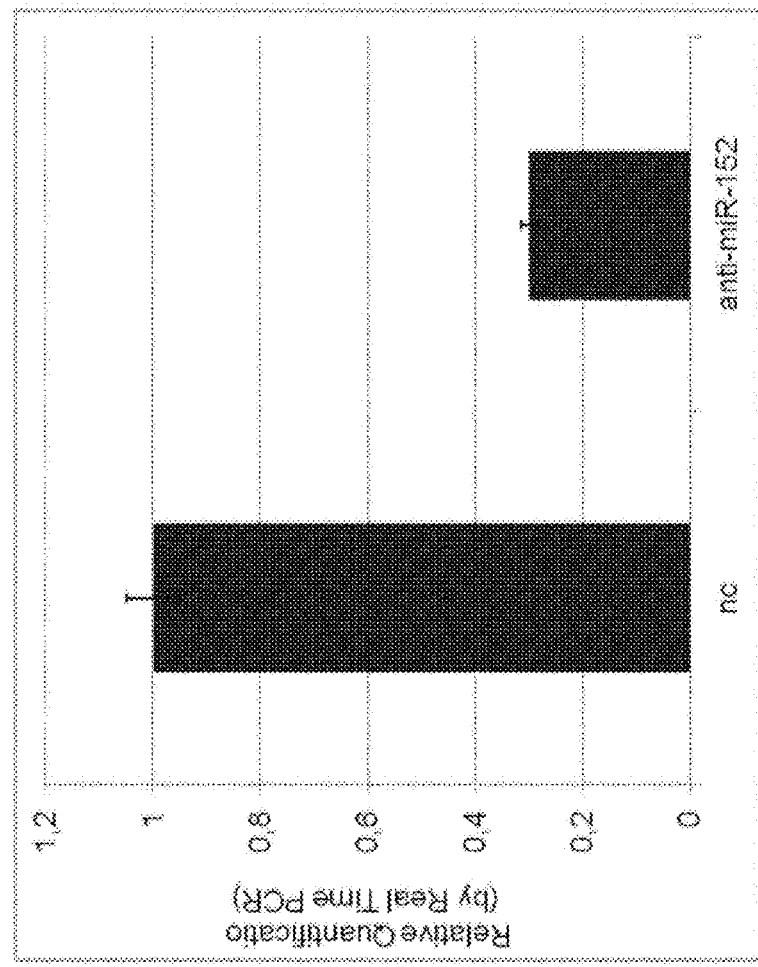

FIG. 11
Inhibition of miR-152 Using Specific AntagomiR in Fibroblasts.

Relative quantification by Real Time PCR of miR-152 level ninety-six hours after transfection of fibroblasts with negative control and anti-miR-152 sequences.

Figure 12:
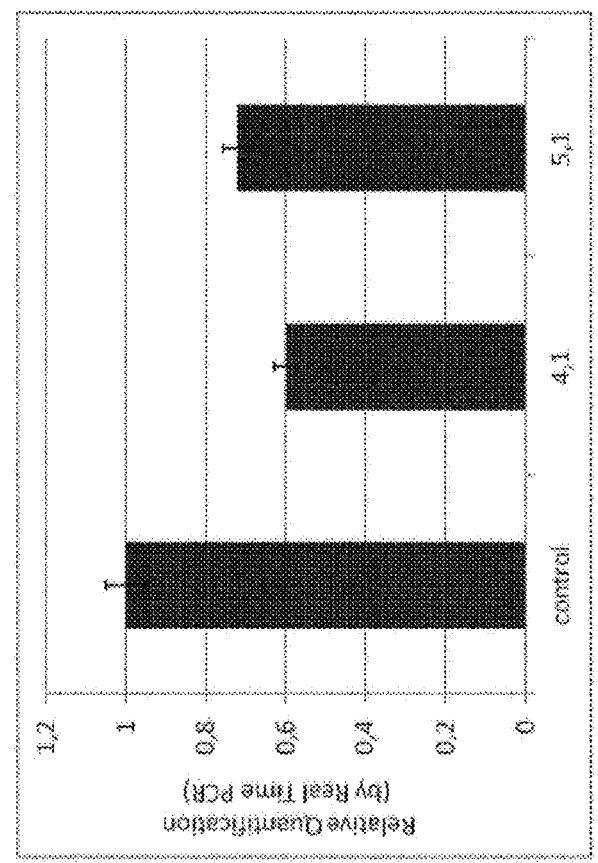

FIG. 12
Inhibition of miR-134 by Compound 4 and 5.

Relative quantification by Real Time PCR of miR-134 level forty-eight hours after treatment of fibroblasts with negative control and compounds 4 or 5 at different concentrations.

Figure 13:
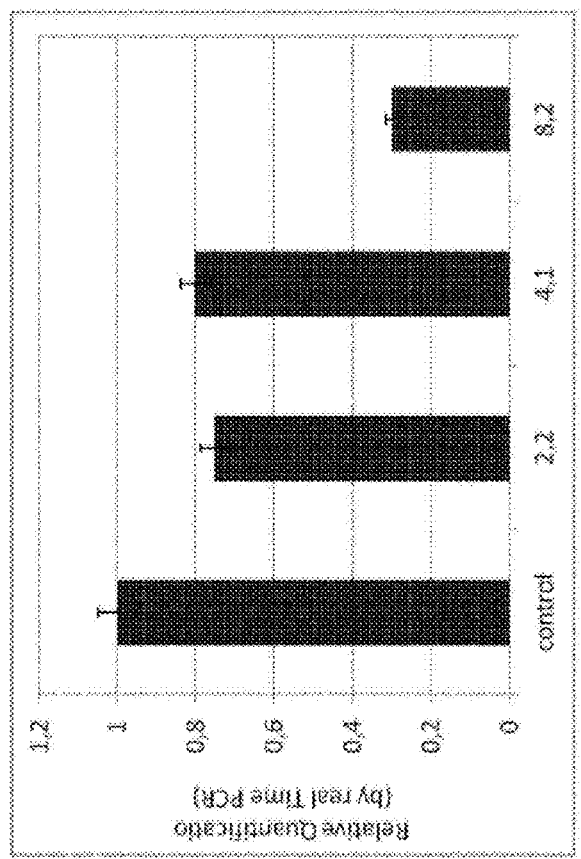

FIG. 13
Inhibition of miR-152 by Compounds 2, 4 and 8.

Relative quantification by Real Time PCR of miR-152 level forty-eight hours after treatment of fibroblasts with negative control and compounds 2, 4 or 8 at different concentrations.

EXAMPLE 1

Material and Methods

Cell Culture and Transfection
Neonatal Human Primary Dermal Fibroblasts (HDFn, Cascade, Invitrogen, Carlsbad, Calif., USA) were cultured in 106 medium added with LSGS growth supplements (Cascade). Cells were passaged usually once a week, at each passage the harvested cells number and seeded cell number were recorded in order to calculate the population doublings occurring between passages and the population doubling time. At each passage different aliquots of the cells were harvested to extract in triplicate RNA and proteins and an aliquot was submitted to senescence activated β-galactosidase staining in order to assay the senescent or non-senescent state of the cells.

Human primary fibroblasts were transfected with human pre-miR 134, anti-miR-134, pre-miR-152, anti-miR-152 and scramble sequence as negative control (Ambion, Tex., USA) using the Lipofecatmine RNAimax transfection reagent (Invitrogen) according to manufacturer protocols. 24 hrs after transfection, the medium was removed and replaced with fresh medium.

400.000 human primary fibroblasts were plated in 106 medium with LSGS growth supplements and treated with test compounds. After 24 and 48 hours cells were collected and mRNA extracted following standard procedures. Real time PCR were performed as described below.

RNA Extraction and Real Time PCR Analysis

Total RNA from cells was isolated using mirVana mirRNA Isolation Kit (Ambion) by following the manufacturer's protocol for total RNA extraction. Total RNA was quantified using a NanoDrop Spectophotometer (Thermo Scientific, Delaware, USA) and RNA quality was controlled on an agarose gel. For microRNA detection, RNA was reverse transcribed using TaqMan MicroRNA Reverse Transcription kit and qRT-PCR was performed with TaqMan universal master mix (Applied Biosystem) and specific primers for miR-134 and miR-152. U18 was used as an internal control (Applied Biosystem). The expression of each gene and miR was defined from the threshold cycle (Ct), and relative expression levels were calculated by using the 2-ΔΔCt method after normalization with reference to the expression of the housekeeping gene U18.

Senescence-Associated β-Galactosidase Staining

Cells were grown in 6-well culture plates, washed with PBS, and fixed with 2% formaldehyde/0.2% glutaraldehyde in PBS for 5 minutes. After another washing step with PBS, cells were incubated with β-galactosidase staining solution (150 mmol/L NaCl, 2 mmol/L $MgCl_2$, 5 mmol/L potassium ferricyanide, 5 mmol/L potassium ferrocyanide, 40 mmol/L citric acid, 12 mmol/L sodium phosphate, pH 6.0, containing 1 mg/mL 5-bromo-4-chloro-3-indolyl-β-Dgalactoside [X-gal]) for 24 hours at 37° C. The reaction was stopped by replacing the staining solution with 70% glycerol.

Cell Proliferation and Cell Cycle Analysis

Methods used to evaluate cell proliferation are generally based on incorporation of thymidine analogues such as 3H thymidine or bromodeoxyuridine (BrdU) during DNA synthesis. The Click-iT™ EdU flow cytometry assay kit is a novel alternative to BrdU assay (Molecular Probes, Eugene, Oreg., USA). This method replaces antibody-based detection of the nucleoside analogue, BrdU, with EdU (5-ethynyl-2'-deoxyuridine), which is a nucleoside analogue of thymidine that is incorporated into DNA during active DNA synthesis. Briefly, cells were incubated with EdU for 4 hrs. After incubation, samples were fixed, permeabilized and stained according to the manufacturer's protocol. Cell cycle was analysed using a FACS Calibur flow cytometer (BD Biosciences, San Jose, Calif., USA). Fifteen thousand events were evaluated using the Cell Quest (BD) and Modfit LT (Verity Software; BD) programs.

Bioinformatics

Analysis of miR-134 and miR-152 target sites on ITGA9 3'UTR were performed using the TargetScan 5.1 software available at http://www.targetscan.org/

Western Blotting

Total cell extracts were resolved on a SDS polyacrylamide gel, blotted on a Hybond P PVDF membrane (G&E Healthcare, UK). Membranes were blocked with PBST 5% non fat dry milk, incubated with primary antibodies for 2 h at room temperature, washed and hybridized for 1 h at room temperature using the appropriate horseradish peroxidase-conjugated secondary antibody (rabbit and mouse, BioRad, Hercules, Calif., USA). Detection was performed with the ECL chemiluminescence kit (Perkin Elmer, Waltham, Mass., USA). anti-Sirt1 (Abcam; dilution 1:500), anti-βactin (Sigma, St Louis, Minn., USA; dilution 1:5000), anti-p16 (Santa Cruz Biotechnology, California, USA; dilution 1:1000), anti-ITGA9 (Sigma, St Louis, Minn., USA; dilution 1:400) were used.

Results

1—Establishment of a Model for Replicative Senescence in Primary Human Fibroblasts.

Human primary fibroblasts were cultured and serially passaged until the reached the senescent state. FIG. 1A is showing the population doublings of primary human fibroblasts during 103 days of culture. After 70 population (passage 16-p16) doublings the growth curve has a plateau, showing that cells stop dividing and are reaching the senescent state. Cells were collected at p1, p4, p8 and p16 to perform western blot analysis p16/INK4a and Sirt-1. Diminished expression of Sirt-1 and increasing levels of p16/INK4a show that cells are entering into the replicative senescent state. β-actin protein levels are reported as a loading control (FIGS. 1A and 1B). Percentage of proliferating cells is diminishing during senescence as shown by the percentage of BrdU positive primary human fibroblasts at different passages (FIG. 1C). Primary human fibroblasts undergo replicative senescence after the 16 passage at 70 population doublings. Photomicrographs of SA-β-galactosidase staining in primary human fibroblasts at different passages show the expression of the senescent marker in older cells. Cells expressing SA-β-galactosidase show a deep blue staining (FIG. 1D), staining quantification is shown in FIG. 1E.

2—miR-134 Levels in Senescing Fibroblasts.

At p1, p11 and p16, cells were collected to perform Real time PCR. Relative quantification of miR-134 levels between p1 and p16 shows significant increase in miR-134 expression in senescent fibroblasts: at p16, miR-134 expression is around 5.35 (±0.08) higher than its expression at p1 (which is equal to 1.00±0.05), FIG. 2. Therefore, the fibroblasts senescent state, but not the fibroblasts proliferating state, is associated with an increase in miR-134 expression.

3—miR-152 Levels in Senescing Fibroblasts.

At p1, p11 and p16, cells were collected to perform Real time PCR. Relative quantification of miR-152 levels between p1 and p16 shows significant increase in miR-152 expression in senescent fibroblasts: at p16, miR-152 expression is around 3.37 (±0.09) higher than its expression at p1 (which is equal to 1.00±0.07), FIG. 3. Therefore, the fibroblasts senescent state, but not the fibroblasts proliferating state, is associated with an increase in miR-152 expression.

4—miR-134 and miR-152 Reduce Proliferation in Fibroblasts Upon Transfection in Proliferating/Young Fibroblasts.

Ninety-six hours after transfection of human dermal fibroblasts with a negative control, miR-134 or miR-152 sequences, cells were subjected to a 3 h BrdU pulse, collected, PI-stained, and analyzed by flow cytometry as described in methods. The percentage of proliferating cells is diminishing upon miR-134 and miR-152 transfection as shown by the percentage of BrdU positive primary human fibroblasts transfected with negative control (26%), miR-134 (19%) and miR-152 (18%), FIGS. 4 A and 4B.

5—miR-134 and miR-152 Induce Senescence in Fibroblasts Upon Transfection in Proliferating/Young Fibroblasts.

Upon tranfection with miR-134 and miR-152, SA-β-galactosidase staining increased significantly in fibroblasts, demonstrating that these two miRNAs are sufficient per se to induce senescence (FIG. 5A). Quantification of blue-cell/field of human dermal fibroblasts, ninety-six hours after transfection, indicate that SA-β-galactosidase staining increases of 4-4.5 folds as compared with negative control (FIG. 5B).

6—ITGA9 is a Target of Both miR-134 and miR-152.

We have performed relative quantification by Real Time PCR of ITGA9 mRNA using cells at p1 and p16 (FIG. 6A), the data obtained clearly show that ITGA9 mRNA is strongly reduced in senescent fibroblasts (p16). Indeed, relative quantification by Real Time PCR of ITGA9 mRNA level of human dermal fibroblasts ninety-six hours after transfection indicate that ITGA9 is reduced 20% and 40%, respectively, upon miR-134 and miR-152 transfection. This is less evident at protein level (FIG. 6C) in the same experimental condition, probably for ITGA9 high protein stability. Using targetScan 6.1 software, we have identified on ITGA9 3'UTR two predicted, for miR-134 and miR-152, target sites. ITGA9 mRNA is downregulated upon miR-134 and miR-152 transfection in fibroblasts as indicated in FIG. 7.

7—ITGA5 is a Target of miR-152.

We have performed relative quantification by Real Time PCR of ITGA5 mRNA using cells at p1 and p16 (FIG. 8A), the data obtained clearly show that ITGA5 mRNA is reduced in senescent fibroblasts (p16). Indeed, real Time PCR of ITGA5 mRNA level of human dermal fibroblasts ninety-six hours after transfection indicate that ITGA5 is reduced 30%, upon miR-152 transfection. This is also evident at protein level (FIG. 8C) in the same experimental condition. Using targetScan 6.1 software, we have identified on ITGA5 3'UTR two predicted target sites for miR-152. Upon transfection, ITGA5 is downregulated by miR-152 in fibroblasts as shown by the relative quantification by Real Time PCR of ITGA5 mRNA level of human fibroblasts. Western blots performed on protein extracts from human fibroblasts after miR-152 and anti-miR-152 transfection showed a significant decrease of ITGA5. β-Actin was used as loading control.

8—Modulation of miR-134 by Synthetic Anti-miR-134.

Anti-miRNAs are miRNA inhibitors that specifically inhibit endogenous miRNAs. Anti-miRNAs are single stranded nucleic acids designed to specifically bind to and inhibit endogenous microRNA molecules. Anti-miRNAs have nucleic sequence complementary to the sequence of the target miRNA. These ready-to-use inhibitors can be introduced into cells using transfection or electroporation parameters similar to those used for siRNAs, and enable detailed study of miRNA biological effects. Use of the anti-miRNA enables miRNA functional analysis by downregulation of miRNA activity. Anti-miRNAs are commercially available; they can for example be obtained by Ambion or Applied Biosystems. Primary human fibroblasts were treated with an anti-miR-134 at different concentrations. After 96 hours cells were harvested for relative quantification of miR-134 levels using Real time PCR. The anti-miR-134 is significantly downregulating miR-134 levels with respect to the untreated cells; the expression of miR-134 in treated cells is only 0.184±0.022 (whereas it is 1.00±0.01 for scramble) (FIG. 10).

9—Modulation of miR-152 by Synthetic Anti-miR-152.

Anti-miRNAs are miRNA inhibitors that specifically inhibit endogenous miRNAs. Anti-miRNAs are single stranded nucleic acids designed to specifically bind to and inhibit endogenous microRNA molecules. Anti-miRNAs have nucleic sequence complementary to the sequence of the target miRNA. These ready-to-use inhibitors can be introduced into cells using transfection or electroporation parameters similar to those used for siRNAs, and enable detailed study of miRNA biological effects. Use of the anti-miRNA enables miRNA functional analysis by downregulation of miRNA activity. Anti-miRNAs are commercially available; they can for example be obtained by Ambion or Applied Biosystems. Primary human fibroblasts were treated with an anti-miR-152 at different concentrations. After 96 hours cells were harvested for relative quantification of miR-152 levels using Real time PCR. The anti-miR-152 is significantly downregulating miR-152 levels with respect to the untreated cells; the expression of miR-152 in treated cells is only 0.325±0.032 (whereas it is 1.00±0.01 for scramble) (FIG. 11).

10—Inhibition of miR-134 by Compounds 4 and 5.

Primary human fibroblasts were treated with compounds 4 and 5, respectively Epigallocatechine Gallate and Verbascoside, at the concentration indicated in FIG. 12. After 48 hours cells were harvested for relative quantification of miR-134 levels using Real time PCR. The compounds 4 and 5 are significantly downregulating miR-134 levels with respect to the untreated cells; the expression of miR-134 in treated cells is only 0.603±0.03 and 0.734±0.05 (whereas it is 1.00±0.01 for scramble) (FIG. 12).

11—Inhibition of miR-152 by Compounds 2, 4 and 8.

Primary human fibroblasts were treated with compounds 2, 4 and 8, respectively Catechine Hydrate, Epigallocatechine Gallate and Bois d'Ange PFA, at the concentration indicated in FIG. 13. After 48 hours cells were harvested for relative quantification of miR-152 levels using Real time PCR. The compounds 2, 4 and 8 are significantly downregulating miR-152 levels with respect to the untreated cells; the expression of miR-152 in treated cells is only 0.769±0.03, 0.804±0.05 and 0.314±0.04 (whereas it is 1.00±0.01 for scramble) (FIG. 13).

EXAMPLE 2

Cosmetic Composition (O/W Serum)

The following composition may be prepared in a classical manner for the man skilled in the art.

The active agent is prepared as follows:

The wood of *Andira coriacea* (i.e. Bois d'Ange) was extracted with ethanol, yielding 386 mg of crude extract after evaporation under reduced pressure. The crude extract was then purified by reverse phase preparative HPLC(C18 Varian Pursuit XRS, 250 mm×41.1 mm×5 nm) using a gradient of H2O+0.1% formic acid and MeOH (from H2O+FA/MeOH 70:30 to 60:40 in 17 min at 60 mL min-1) to afford pure Coatline A (12.3 mg) and Coatline B (40.2 mg).

| INCI name | % (w/w) |
|---|---|
| Water | QSP 100.00 |
| Chelating agent | 0.05 |
| pH balance | 0.05 |
| Preservatives | 0.05 |
| Glycol | 3.25 |
| AMMONIUM ACRYLOYLDIMETHYLTAURATE/VP COPOLYMER | 1.20 |
| ACRYLATES/C10-30 ALKYL ACRYLATE CROSSPOLYMER | 0.20 |
| GLYCERIN | 3.00 |
| GLYCERYLPOLYMETHACRYLATE | 4.18 |
| SODIUM ACETYLATED HYALURONATE | 0.05 |
| Oil | 10.00 |
| ALCOHOL | 8.00 |

-continued

| INCI name | % (w/w) |
|---|---|
| PERFUMES | 0.30 |
| Coatlines obtained as described above | 0.05 |

REFERENCES

Serrano et al (1997), Cell 88:593-562
Campisi (2001), Trends Cell Biol 11:S27-S31
Schmitt et al (2002) Cell 109:335-346
Narita et al (2003), Cell 113:703-706
Sharpless et al (2004) J Clin Invest 113:160-168
Grillari et al (2010) Exp Gerontol 45: 302-311
Hackl et al. (2010) Aging Cell 9: 291-296
Lafferty-Whyte K et al (2009) Biochim Biophys Acta 1792: 341-352
He L et al. (2007) Nature 447: 1130-1134
Maes O C et al (2009) J Cell Physiol 221: 109-119
Faraonio R et al (2012) Cell Death Differ. 19(4):713-21
Dhahbi et al (2011) PLoS One. 6(5):e20509
Tsuruta et al (2011) Cancer Research. 71(20):6450-62
Huang et al, (2010) Hepatology. 52(1):60-70
Quan T et al, (2009) J Investig Dermatol Symp Proc. 14(1):20-4
Roy S et al, (2011) J Oral Pathol Med. 40(10):755-61

The invention claimed is:

1. An in vitro method for screening for candidate compounds for attenuating ageing of the skin, comprising the following steps:
   (a) bringing at least one test compound in contact with at least one sample of fibroblasts;
   (b) measuring the expression or the activity of at least one microRNA chosen from miR-134 and miR-152 in said fibroblasts;
   (c) selecting the compounds for which an inhibition of at least 20% of the expression, or an inhibition of at least 20% of the activity, of said at least one microRNA is measured in the fibroblasts treated in step (a) compared with untreated fibroblasts.

2. The method according to claim 1, wherein step (b) is performed before and after step (a).

3. The method according to claim 1, wherein the test compounds are chosen from botanical extracts.

4. The method according to claim 1, wherein the inhibition of expression or activity of the microRNA measured in step (c) is at least 50%.

5. The method according to claim 1, wherein the inhibition of expression or activity of the microRNA measured in step (c) is at least 40%.

6. The method according to claim 1, wherein the inhibition of expression or activity of the microRNA measured in step (c) is at least 60%.

7. The method according to claim 1, wherein the at least one microRNA in step (b) is miR-134.

8. The method according to claim 1,
   wherein said fibroblasts are pre-senescent fibroblasts that have been obtained after 70 population doublings in classical culture conditions,
   wherein the classical culture conditions comprise culturing the fibroblasts in 106 medium added with LSGS growth supplements, and constantly keeping the fibroblasts in a subconfluent state.

9. The method according to claim 1, wherein said fibroblasts are pre-senescent fibroblasts.

10. The method according to claim 9, wherein the pre-senescent fibroblasts are obtained after 70 population doublings in classical culture conditions.

11. The method according to claim 10, wherein the classical culture conditions comprise culturing the fibroblasts in 106 medium added with LSGS growth supplements, and constantly keeping the fibroblasts in a subconfluent state.

12. An in vitro method for screening for candidate compounds for attenuating ageing of the skin, comprising the following steps:
   (a') preparing at least two samples of fibroblasts;
   (a) bringing at least one test compound into contact with at least one of said at least two samples of fibroblasts, while leaving at least one of said two samples of fibroblast untreated; then
   (b) measuring the expression or the activity of at least one microRNA chosen from miR-134 and miR-152 in said at least two samples of fibroblasts; and
   (c) selecting the compounds for which an inhibition of at least 20% of the expression, or an inhibition of at least 20% of the activity, of said at least one microRNA is measured in the at least one sample of fibroblasts brought into contact with the at least one test compound treated in step (a) compared with the sample of untreated fibroblasts.

* * * * *

```
                          SEQUENCE LISTING

<160> NUMBER OF SEQ ID NOS: 7

<210> SEQ ID NO 1
<211> LENGTH: 22
<212> TYPE: RNA
<213> ORGANISM: Homo sapiens

<400> SEQUENCE: 1
ugugacuggu ugaccagagg gg                                                22

<210> SEQ ID NO 2
<211> LENGTH: 21
<212> TYPE: RNA
<213> ORGANISM: Homo sapiens

<400> SEQUENCE: 2
ucagugcaug acagaacuug g                                                 21

<210> SEQ ID NO 3
<211> LENGTH: 18
<212> TYPE: RNA
<213> ORGANISM: Homo sapiens

<400> SEQUENCE: 3
gcugccacac cagucaca                                                     18

<210> SEQ ID NO 4
<211> LENGTH: 22
<212> TYPE: RNA
<213> ORGANISM: Homo sapiens

<400> SEQUENCE: 4
ggggagacca guuggucagu gu                                                22

<210> SEQ ID NO 5
<211> LENGTH: 23
<212> TYPE: RNA
<213> ORGANISM: Homo sapiens

<400> SEQUENCE: 5
auauaauuca cucaagcacu gau                                               23

<210> SEQ ID NO 6
<211> LENGTH: 21
<212> TYPE: RNA
<213> ORGANISM: Homo sapiens

<400> SEQUENCE: 6
gguucaagac aguacgugac u                                                 21
```

```
<210> SEQ ID NO 7
<211> LENGTH: 46
<212> TYPE: RNA
<213> ORGANISM: Homo sapiens

<400> SEQUENCE: 7
gaucccuccc ccccaugcac uguguucugc cugccagcug cacuga                    46
```